United States Patent [19]

Roginski

[11] Patent Number: 4,962,041
[45] Date of Patent: Oct. 9, 1990

[54] METHOD AND APPARATUS FOR AUTOMATIC PROCESSING AND ANALYZING OF BLOOD SERUM

[75] Inventor: Edward T. Roginski, Hamtramck, Mich.

[73] Assignee: Medical Automation Specialities, Inc., Hamtramck, Mich.

[21] Appl. No.: 330,151

[22] Filed: Mar. 29, 1989

Related U.S. Application Data

[63] Continuation-in-part of Ser. No. 254,420, Oct. 6, 1988.

[51] Int. Cl.$^5$ .................. G01N 27/02; G01N 33/48
[52] U.S. Cl. ...................... 436/150; 422/63; 324/687; 324/697
[58] Field of Search .............. 436/43, 45, 50, 54, 436/70, 150; 324/61 P, 61 R, 687, 697; 422/63

[56] References Cited

U.S. PATENT DOCUMENTS

| | | | |
|---|---|---|---|
| 3,918,913 | 11/1975 | Stevenson | 436/43 |
| 3,971,630 | 7/1976 | Sandrock | 436/45 |
| 4,487,836 | 12/1984 | Takayanagi | 436/150 |
| 4,788,150 | 11/1988 | Nelson | 422/63 |
| 4,818,492 | 4/1989 | Shimizu | 422/63 |

Primary Examiner—Reinhard J. Eisenzopf
Assistant Examiner—Jose M. Jolis
Attorney, Agent, or Firm—Krass and Young

[57] ABSTRACT

A method and apparatus for processing and analyzing blood serum includes a capacitive sensing unit for receiving centrifuged test tubes and generating output signals indicative of the boundary position between the separator gel and the blood serum in the tubes, and a computer connected to the sensing unit to receive and analyze the output signals of the capacitive sensing unit. An aspirator/dispenser needle and retainer probe unit is positioned above the sensing unit and is capable of lowering a needle; under the control of the computer, to puncture the stopper of a test tube and then withdraw blood serum. The retainer probe prevents the withdrawal or loosening of the tube stopper upon withdrawal of the needle from the tube. A color sensor inspects the aspirated sample and determines whether it is suitable for analysis.

15 Claims, 2 Drawing Sheets

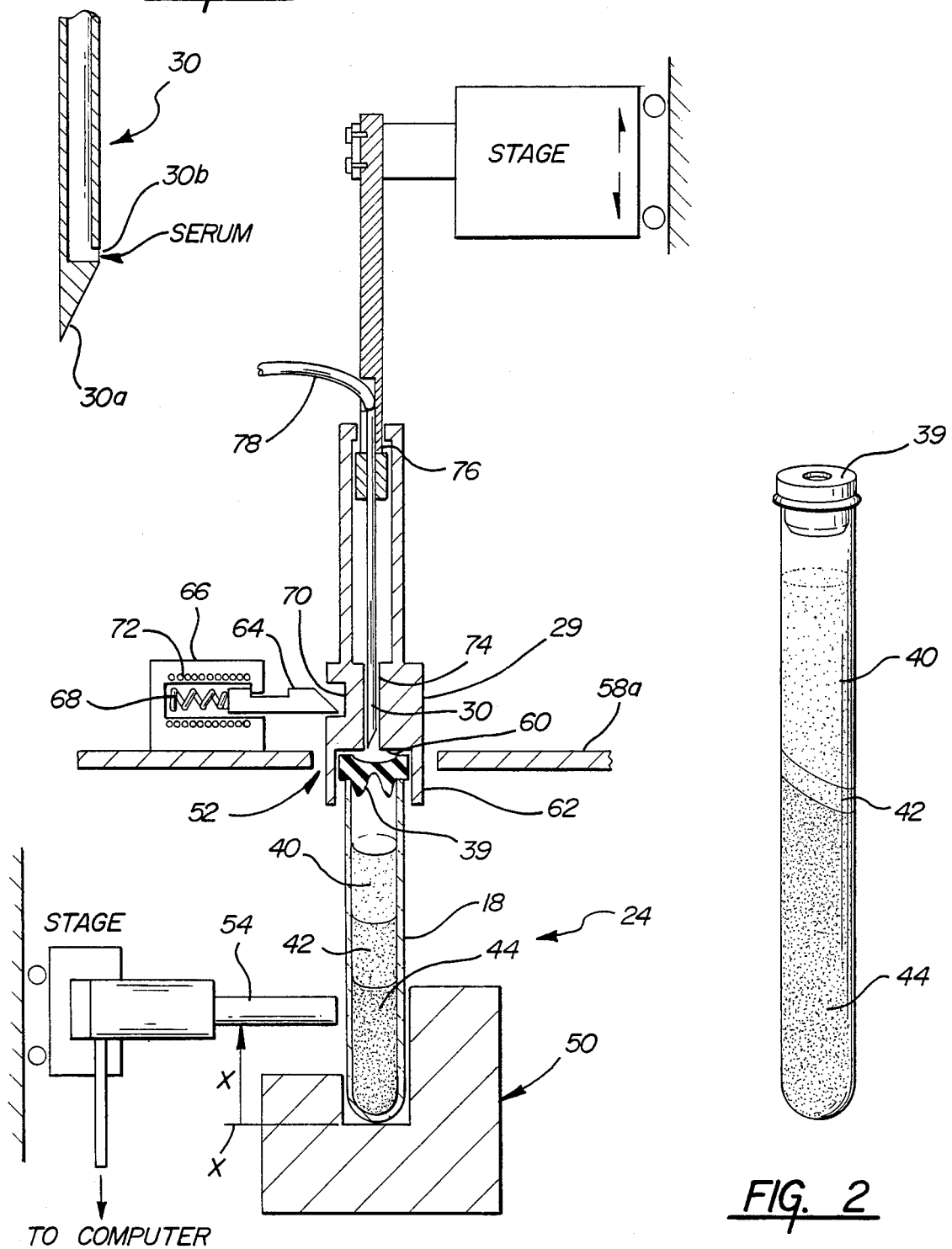

METHOD AND APPARATUS FOR AUTOMATIC PROCESSING AND ANALYZING OF BLOOD SERUM

BACKGROUND OF THE INVENTION

This application is a continuation-in-part of U.S. patent application Ser. No. 254,420 filed Oct. 6, 1988.

A. FIELD OF THE INVENTION

This invention relates to apparatus and a method for non-invasively determining the location of blood serum boundaries in sealed test tubes that have been centrifuged to separate the serum from whole blood cells.

B. DESCRIPTION OF RELATED ART

The process of separating the red blood cells from the blood serum of a whole blood specimen by centrifuge and then removing the blood serum is conducted on a large scale in hospitals and laboratories. This process is usually conducted manually by a technician. In the process, a stopper sealed test tube, containing a whole blood specimen and a separating gel, is centrifuged so that its contents are separated into three layers, a top layer containing the serum, a middle layer containing the separating gel, and a bottom layer containing the red blood cells. After the test tube is centrifuged, the technician must examine the blood specimen to determine whether it is defective. If the sample is not defective, the technician then removes the rubber stopper, eyes the placement of the needle in order to insure the needle does not contact the separating gel, and withdraws a sample of the blood serum from the top layer and places the sample into a cup. Pouring the sample from the opened tube and pipetting are also common practices. Efficiency, accuracy, and maintaining the integrity of the blood specimen are essential to this process. More important is the safety of the technician while completing the process. By fully automating this process, these factors are greatly enhanced and the danger to the technician of being exposed to any transmitted diseases in the specimens during this process is greatly reduced.

U.S. Pat. Nos. 4,713,974 and 4,478,095 disclose devices for automatically piercing container lids and withdrawing samples. Neither of these patents disclose any means for sensing an appropriate level inside the test tube for positioning the tip of the sampling needle. Also, these patents do not disclose devices for use with centrifuged blood samples.

U.S. Pat. Nos. 4,120,662 and 4,311,484 both disclose blood sample processing systems for delivering blood from closed vacutainers to a Coulter Counter. These systems are not suitable for use with centrifuged blood samples in that tubes are sampled in an approximately horizontal position and are agitated prior to sampling.

U.S. Pat. No. 4,326,851 discloses a level sensor for use with a fluid transfer mechanism for determining when the bottom tip of a fluid aspirating probe touches the top surface of a sample fluid. This device cannot be used with blood samples in conventional stoppered test tubes.

Copending application U.S. Ser. No. 254,420 discloses an apparatus and method for automatically centrifuging blood specimens and separating gels in stopper sealed test tubes, determining whether the centrifuged specimens are defective, and removing and then dispensing blood serum samples from only those sealed test tubes in which the specimens are not defective. This system photoelectrically determines whether the sample is defective and where the boundary of the centrifuged separator gel and blood serum lies in the test tube. A problem arises, however, when the test tubes are provided on their outer surface with adhesive data labels or other materials which partially or fully block the transmission of light through the test tube, thereby preventing the photoelectric system from determining the location of the separator gel/blood serum boundary.

C. SUMMARY OF THE INVENTION

This invention is accordingly directed toward a method and apparatus for non-invasively, non-visually determining the location of the separator/serum boundary in centrifuged test tubes containing separate layers of blood serum, separator gel or wax and blood cells. The method and apparatus of the present invention is effective even if the test tubes are partially or fully covered by labels or other materials which hinder or block the transmission of light therethrough.

The method of the present invention includes placing the test tube into a capacitive sensing unit, and analyzing the electrical signals generated by the capacitive sensing unit to determine the position of the boundary surface between the separator gel and the blood serum.

The method of the present invention further includes withdrawing a sample of the serum from the test tube with a needle and photoelectrically testing the color of the serum to determine whether it has been successfully separated and can accordingly be properly analyzed. The method also includes maintaining the test tube stopper in tight sealing engagement with the test tube upon withdrawal of the needle.

In one embodiment, a capacitive sensor probe is moved longitudinally adjacent and along a test tube in the sensing unit. The capacitive sensor probe is connected to a computer and generates output signals corresponding to the dielectric constant of the tube contents and the position of the probe relative to a reference point on the tube. The position of the boundary surface between the separator gel and the blood serum is determined by identifying the longitudinal position of the probe relative to the tube when the rate of change of the output signal corresponding to the dielectric constant of the tube contents is at a maximum.

In the illustrated embodiment, the sensing unit includes a vertical cavity operative to receive a test tube. The sensing unit further includes a capacitive sensor probe extending generally proximate a test tube placed in the cavity such that the probe acts as one plate of a capacitor and the tube and its contents the other plate. The probe is mounted within the sensing unit for longitudinal movement generally parallel to the tube axis. The capacitive sensor probe emits output signals corresponding to the dielectric constant of the tube contents and the position of the probe relative to a reference point on the tube. The apparatus of the present invention further includes means for receiving these electrical output signals and analyzing them to determine the position of the boundary surface between the separator wax and the blood serum along the longitudinal axis of the tube.

The apparatus further includes a needle apparatus, responsive to the means for determining the position of the boundary surface between the separator wax and the blood serum, connected to aspirating/dispensing means for insertion into a test tube and for drawing a blood serum sample from the tube.

The apparatus further includes color sensing apparatus operatively associated with the aspirating means to examine the blood serum sample withdrawn from the tube. The color sensing apparatus photoelectrically generates an output signal corresponding to the color of the blood serum, which signal is received by the computer for comparing the signal to reference data to determine whether the sample is defective.

The apparatus also includes retainer apparatus operatively associated with the needle apparatus to retain the tube stopper in the tube when the needle is withdrawn from the tube.

The apparatus also includes a needle for the needle apparatus, which needle is designed to prevent coring of the tube stopper when piercing it and further to minimize carry-over of serum between samples.

The present invention makes the process of centrifuging and analyzing blood specimens efficient and accurate. It also eliminates the danger of a technician being exposed to any transmitted disease, such as HIV or hepatitis B, during the process.

BRIEF DESCRIPTION OF THE DRAWINGS

Other objectives, advantages, and applications of the present invention will be made apparent by the following detailed description of the preferred embodiment of the invention. The description makes reference to the accompanying drawings in which:

FIG. 2 is a cross-sectional view of a test tube, containing a centrifuged blood specimen, of the type used in the present invention;

FIG. 3 is a partial cross-sectional view of the capacitive sensing unit and the aspirator/dispenser needle apparatus and retainer apparatus of the invention;

FIG. 5 is a cross-sectional view of a needle used to withdraw serum sample from a stoppered test tube.

DETAILED DESCRIPTION OF THE PREFERRED EMBODIMENT

Figure 1:
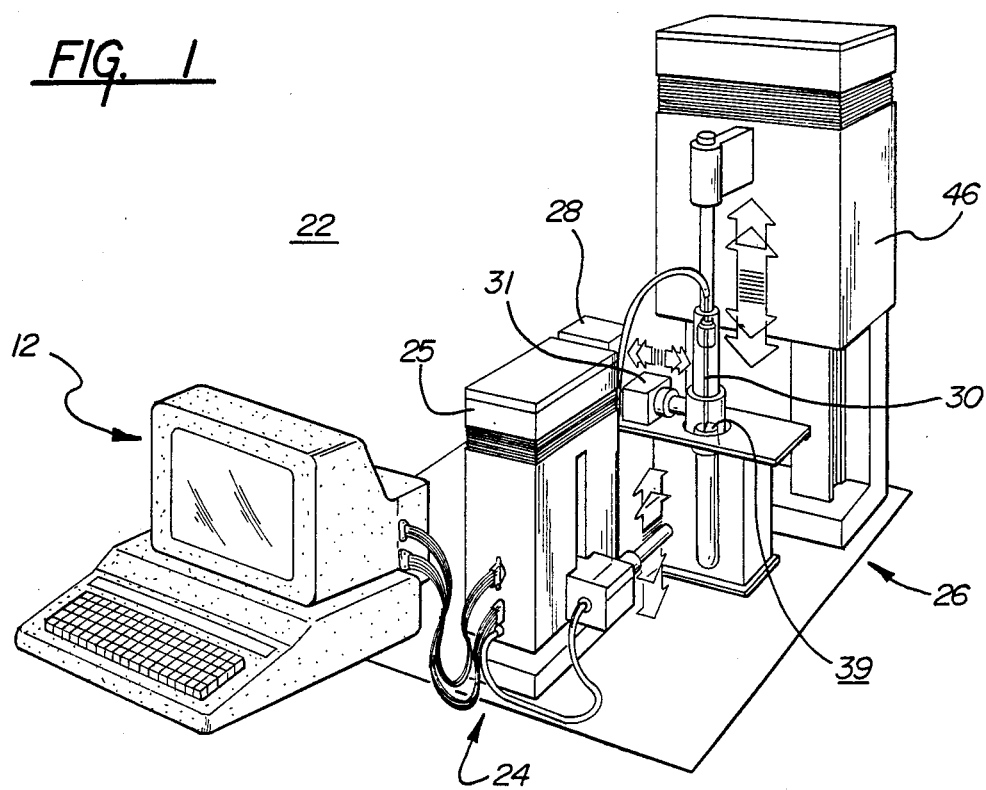
FIG. 1 is a perspective view of the preferred embodiment of the system for capacitively analyzing the contents of the test tube.
Figure 4:
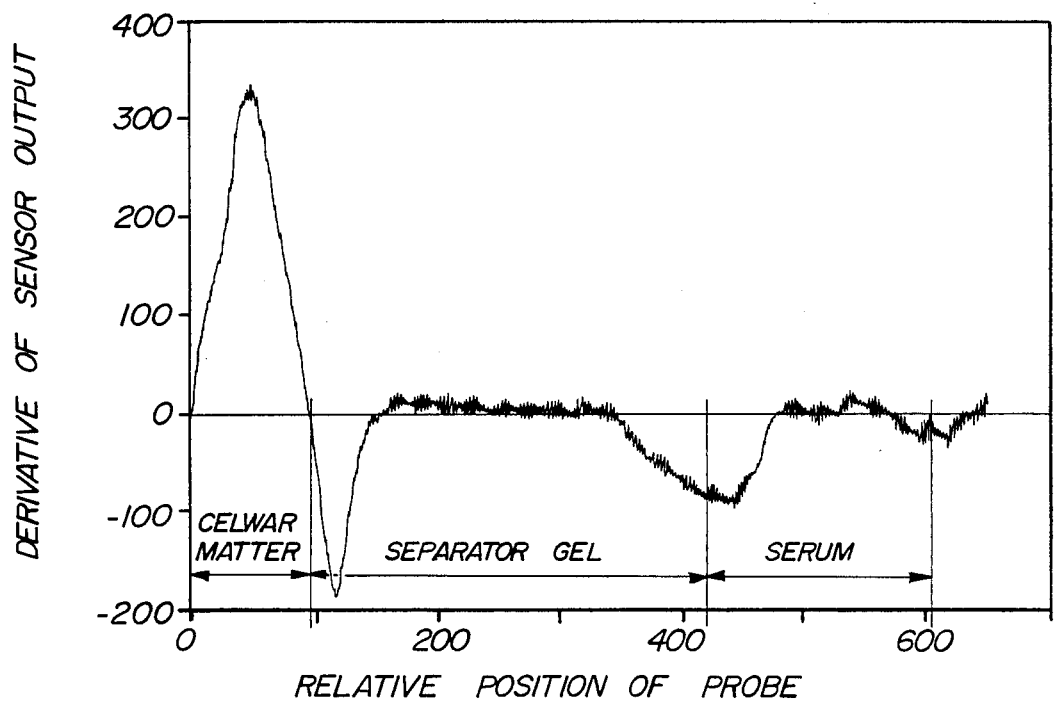
FIG. 4 is a graphical representation of the method used to determine the position of the boundary surface between the/separator gel and the blood serum in a test tube.

Referring to FIG. 1, the preferred embodiment of the present invention comprises a serum sensing and aspirator/dispenser unit, generally indicated at 22. This station includes a capacitive blood serum sensing unit 24, and an aspirator/dispenser unit 26. Both the sensing unit and the aspirator/dispenser unit are connected to a control computer 12, such as a standard PC. The capacitive sensing unit 24 receives test tubes containing centrifuged blood specimens and outputs signals to the computer 12 so that the computer may determine an appropriate level in the test tube to position the tip of an aspirator needle for removing a blood serum sample. The aspirator/dispenser unit 26 functions, under the control of computer 12, to lower a retainer probe 29 and sampling needle 30 to puncture the stopper seal of a test tube held in the sensing unit 24 for withdrawing samples from the test tube.

A centrifuge (not shown) is used to centrifuge whole blood specimens along with separating gels in stopper sealed test tubes by rotating the tubes inclined with respect to a vertical axis about that axis so that the contents of the test tubes are separated, as indicated in FIG. 2, into a top layer 40 containing the blood serum, a middle layer 42 containing the separating gel, and a bottom layer 44 containing the red blood cells. The separator gel (or wax) has a density half-way between the densities of the serum and the red blood cells. As indicated in FIG. 2, after centrifuging the separator gel may not lie in a horizontal plane normal to the longitudinal axis of the test tube, but rather at an angle from the horizontal plane. The orientation of the middle layer 42 is determined by the type of centrifuge used., Centrifuges are well known to the art.

Centrifuged test tubes can be placed in and removed from sensing unit 24 manually or by automatic apparatus under control of computer 12. An example of such automatic apparatus can be found in my copending application Ser. No. 254,420, in which a robotic arm operates under control of a computer to transfer centrifuged test tubes between a photoelectric sensing unit and various input and output stations. Alternatively, a carousel-type feeder unit could be provided to sequentially rotate centrifuged test tubes into and out of capacitive sensing unit 24.

A color sensing unit 28 is connected to photoelectrically scan the blood serum sample withdrawn by aspirator/dispenser unit 26. Color sensor 28 photoelectrically generates an output signal related to the color of the serum, which signal is compared by computer 12 to reference data to determine whether the sample is defective.

The preferred embodiment of the present invention operates, under the control of computer 12, as follows:

First, a centrifuged test tube containing separated layers of serum, separator gel and blood cells is inserted either manually or automatically into the capacitive sensing unit 24, where the location of the blood serum/separator gel boundary is capacitively determined.

Computer 12 next lowers retainer probe 29 into engagement with the test tube stopper 39 by activating a motor in housing 46 connected to one end of a captured internal plunger 48 from which probe 29 depends. Once the retainer probe engages stopper 39, a latching mechanism 31 latches probe 28 into place. Sampling needle 30 located within probe 28 is next lowered to puncture the stopper and descend to the level in the test tube previously determined by the analysis of the output signals from capacitive sensing unit 24. A sample of the blood serum is drawn from the test tube through needle 30 by the aspirator/dispenser unit. In the preferred embodiment of the invention, approximately 1.5 milliliters of serum is withdrawn.

The withdrawn sample of blood serum contained in the aspirator/dispenser tubing 78 is examined by color sensor 28. If the signals from the color sensor indicate that the centrifuged serum sample is too lipemic (white), hemolyzed (red) or otherwise an unsuccessful specimen, then the withdrawn sample and the test tube are disposed of in a suitable manner.

FIG. 3 is a cross-sectional view of the capacitive sensing unit 24 of the preferred embodiment of the present invention. The sensing unit 24 includes a vertical cavity in support block 50. The vertical cavity is open on one side to the exterior of block 50 and is adapted to receive a test tube of conventional construction such that substantially the entire length of one side of the tube is exposed. The vertical cavity also communicates with an opening 52 formed in upper surface 58a of frame 58 containing block 50. Block 50 can be integral with frame 58 or removable therefrom. The sensing unit 24 is connected to a suitable power source (not shown).

A capacitive sensor probe 54 is connected to a motor in housing 25 for vertical reciprocating movement by way of any suitable well-known drive mechanism, for example a stationary screw. After test tube 18 has been positioned within the cavity, capacitive sensor probe 54 is moved under command of computer 12 along the longitudinal axis of the tube from top to bottom. A constant air-space clearance is maintained between the probe and the tube. Capacitive sensor probe 54 contains a capacitive sensor (not shown) and generates output signals corresponding to the dielectric constant of the contents of that portion of the tube adjacent the end of the probe and to the longitudinal position of the probe relative to a reference point "X" on the test tube. These output signals, i.e. the voltage output of the sensor and the position of the probe relative to reference point "X" on the test tube, constitute inputs to a computer algorithm which uses this ordered pair of data to identify the contents and position of content changes in the test tube.

The output of the capacitive sensor probe 54 is determined by both the distance to the tube and the dielectric constant of its contents. However, since the distance between the test tube and the capacitive sensor probe is held constant, the only changes in electrical output are due to variations in the contents of the test tube, such as the transitions between the air, serum 40, separating gel 42, and blood cellular matter 44 in the tube. A specialized processing algorithm in computer 12 is used to determine the location of the separated layers, searching for transitions in the test tube contents by taking the derivative of the voltage output of the capacitive sensor probe 54 and plotting it against the position of probe 54 relative to reference point "X" on the test tube as shown in FIG. 3. The relative maxima and minima in the derivative indicate where the content transitions take place, due to the greatest changes in capacitance being at the points of separation.

In FIG. 3, retainer apparatus is in use with a test tube being capacitively inspected in sensing unit 24. The test tube 18 rests in the cavity below the upper surface 58 of support block 50 while capacitive sensor probe 54 delivers output signals to computer 12 to determine the position of the boundary of separator gel 42 and blood serum 40 in the tube.

The hollow, substantially cylindrical probe body 28, mounted for vertical movement essentially along the axis of the tube, is then lowered under control of computer 12 until inner shoulder 60 is seated on tube stopper 39. Peripheral annular flange 62 extends down and over a portion of the upper end of the tube to firmly restrain the tube. As probe body 28 descends, a solenoid 72 is activated by computer 12 to retract latch 64 back into latch housing 66 against the action of spring 68. When probe body 28 descends to the point where shoulder 60 engages the tube stopper 39, solenoid 72 is turned off, releasing latch 64 into recess 70 of the probe body under the action of spring 68. Latch 64 effectively prevents any upward motion of probe body 28 while the latch is in recess 70. Alternatively, latch 64 can be forced into housing 66 upon the descent of probe body 28 by the action of annular flange 62 on the beveled surface of latch 64.

When computer 12 has determined the location of the serum/separator boundary in response to the output of capacitive sensor probe 54, sampling needle 30 is lowered through an internal channel 74 in the probe body by internal plunger 76, piercing the tube stopper and entering the serum a distance determined by the computer, stopping prior to the serum/separator boundary. A serum sample is then aspirated through needle 30 and tubing 78 connected to the needle's far end. Tubing 78 is connected at the other end to the aspirator/dispenser unit and color sensor (not shown).

It is to be understood that probe 28 can be lowered into its latched position before, during or after the computer 12 determines the location of the serum/separator boundary, as long as needle 30 is lowered after the boundary has been determined. It should also be understood that the distance at which needle 30 is stopped from the serum/separator boundary can be adjusted according to the operator's preference by reprogramming computer 12.

After the sample has been aspirated, plunger 76 and needle 30 are retracted back up into the probe body. The action of the latching mechanism and shoulder 60 retains the stopper to prevent inadvertent loosening or removal of the stopper due to the friction of the withdrawing needle. After the needle has been completely withdrawn from the tube, solenoid 72 retracts the latch, and probe body 28 is lifted out of engagement with the tube and stopper by the continued upward motion of plunger 76.

Referring now to FIG. 5, the structure of needle 30 can be clearly seen. The piercing point 30a of the needle is solid to prevent coring of the stopper, and the aspiration/dispensing port 30b is formed in the side wall of the needle immediately adjacent the inner surface of solid point 30a. This prevents serum from collecting in the probe where it cannot be aspirated or dispensed. This feature, along with the wiping action of the stopper 39 on the exterior of needle 30 upon withdrawal, minimizes carry-over of serum between samplings.

The needle 30 is further preferably provided with a titanium nitride coating, which has been found to greatly reduee wear and maintain the integrity of the needle during prolonged use.

Referring back to FIG. 1, the success of the separation can be determined by further aspirating the sample through tube 78 from needle 30 (not shown) adjacent color sensor 28 to determine the color of the serum sample. The color sensor comprises a light emitting diode positioned to shine light onto the serum contained in the tube, which is preferably transparent, and a phototransistor which receives the light reflected from the sample. The phototransistor generates an analog output signal which is sent to computer 12 and compared with reference data stored therein.

If the sample is determined to be good, i.e. properly separated, it will be dispensed in a suitable manner. If the sample is determined to be lipemic (white), hemolyzed (red) or otherwise defective (yellow), the sample is disposed of in a suitable manner. The associated test tube is then removed from capacitive sensing unit 24 and a new one is inserted.

The above description is not intended to limit the present invention. It is understood that it is possible to make modifications and variations in light of the above teachings without departing from the present invention.

Having thus described my invention, I claim:

1. A method for inspecting a test tube containing a layer of blood cells, a layer of separator gel and a layer of blood serum so as to ascertain the relative position of said layers, the method comprising:
   supporting the test tube;
   providing a capacitive sensor probe operative to provide an output signal corresponding to the dielectric constant of a material proximate thereto;
   providing relative motion between the sensor probe and the test tube, while maintaining the sensor probe at a fixed distance from the test tube;
   providing signalling means for generating positional signals indicative of the position of the sensor probe relative to the test tube;
   analyzing the signals from the sensor probe and the signalling means and correlating changes in the sensor probe output signal with the position of the sensor probe relative to the test tube.

2. A method as in claim 1, including the further step of determining the value of the derivative of the output signal of the sensor probe as said relative motion is provided.

3. A method as in claim 1, including the further steps of:
   providing an aspirator/dispenser unit operative to withdraw and transfer a portion of the contents of the test tube; and
   controlling the aspirator/dispenser unit in response to the signals received by the analyzer, so that the aspirator/dispenser unit withdraws a portion of only a selected one of said layers.

4. A method as in claim 3 including the further step of sensing the color of the withdrawn portion.

5. A method as in claim 1, wherein establishing relative motion between the sensor probe and the test tube comprises disposing the test tube in a support member and moving the sensor probe along the length of the test tube.

6. A method as in claim 3 including the further step of disposing a retainer probe in contact with the test tube so as to engage and support the test tube while the aspirator/dispenser unit is withdrawing the portion of the selected one of said layers.

7. An apparatus for inspecting a test tube containing a layer of blood cells, a layer of separator gel and a layer of blood serum so as to ascertain the relative positions of said layers, the apparatus including:
   means for supporting the test tube;
   a capacitive sensor probe operative to provide an output signal corresponding to the dielectric constant of a material proximate said sensor probe;
   means for supporting the sensor probe at a fixed distance from the test tube;
   means for providing relative motion between the sensor probe and the tube; and
   an analyzer in electrical communication with the sensor probe and with the means for establishing relative motion, said analyzer operative to correlate changes in the output signal provided by the sensor probe with the position of the sensor probe relative to the test tube, whereby said changes are indicative of a change in the dielectric constant, and hence a change in the identity, of the contents of the tube proximate the sensor probe.

8. An apparatus as in claim 7, wherein said analyzer is further operative to determine the value of the derivative of the output signal as relative motion is provided between the sensor probe and the test tube, whereby a derivative value other than zero is indicative of a change in the dielectric constant of the contents of the test tube and hence an interface between two of said layers.

9. An apparatus as in claim 7, wherein said analyzer includes a programmed computer.

10. An apparatus as in claim 7, further including an aspirator/dispenser unit for withdrawing and transferring the contents of the test tube, said unit in operative communication with, and controlled by, the analyzer so as to controllably withdraw a portion of a selected one of said layers.

11. An apparatus as in claim 10, wherein said aspirator/dispenser unit includes a hollow needle having a solid point and a port disposed in the side wall of the needle and in communication with the hollow interior thereof.

12. Apparatus as in claim 10 further including color sensing means associated with the aspirator/dispenser unit and operative to generate a signal corresponding to the color of the withdrawn portion of the selected one of said layers.

13. Apparatus as in claim 7, wherein said means for providing relative motion between the sensor probe and the tube comprises means operative to move the sensor probe along the length of the test tube at a fixed distance therefrom.

14. Apparatus as in claim 10, further including a retainer probe operative to engage and support the test tube when the aspirator/dispenser unit is withdrawing said portion of the selected one of said layers.

15. The apparatus as in claim 10, wherein said aspirator/dispenser includes a hollow needle which is coated with a layer of titanium nitride.

* * * * *